(12) United States Patent
Duffy et al.

(10) Patent No.: US 11,647,980 B2
(45) Date of Patent: May 16, 2023

(54) METHODS FOR NEEDLE IDENTIFICATION ON AN ULTRASOUND DISPLAY SCREEN BY DETERMINING A META-FRAME RATE OF THE DATA SIGNALS

(71) Applicant: Avent, Inc., Alpharetta, GA (US)

(72) Inventors: Shane A. Duffy, Irvine, CA (US); Hakan J. Yazarel, Lake Forest, CA (US); Shirzad Shahriari, Irvine, CA (US); Marc Comtois, Irvine, CA (US); Tingting Wang, Irvine, CA (US); Jamie Collin, Cambridge (GB); Andrew Polijanczuk, Hemingford Grey (GB); Henry Gomersall, Cambridge (GB)

(73) Assignee: Avent, Inc., Alpharetta, GA (US)

( * ) Notice: Subject to any disclaimer, the term of this patent is extended or adjusted under 35 U.S.C. 154(b) by 490 days.

(21) Appl. No.: 16/233,680

(22) Filed: Dec. 27, 2018

(65) Prior Publication Data
US 2020/0205775 A1    Jul. 2, 2020

(51) Int. Cl.
*A61B 8/08* (2006.01)
*A61B 5/06* (2006.01)
(Continued)

(52) U.S. Cl.
CPC ............ *A61B 8/0841* (2013.01); *A61B 5/061* (2013.01); *A61B 8/4245* (2013.01);
(Continued)

(58) Field of Classification Search
CPC ....... A61B 8/0841; A61B 34/20; A61B 5/061; A61B 8/4245; A61B 8/4444–4494;
(Continued)

(56) References Cited

U.S. PATENT DOCUMENTS

| 4,249,539 A | * | 2/1981 | Vilkomerson ....... A61B 8/0841 600/461 |
| 4,576,181 A | | 3/1986 | Wallace et al. |

(Continued)

FOREIGN PATENT DOCUMENTS

| EP | 1 568 324 A2 | 8/2005 |
| EP | 1 652 471 A1 | 5/2006 |

(Continued)

OTHER PUBLICATIONS

Yoon S, Kim MG, Williams JA, et al. Dual-element needle transducer for intravascular ultrasound imaging. J Med Imaging (Bellingham). 2015;2(2):027001. doi:10.1117/1.JMI.2.2.027001 (Year: 2015).*

(Continued)

*Primary Examiner* — Christopher Koharski
*Assistant Examiner* — Richmond J Van Winter
(74) *Attorney, Agent, or Firm* — Dority & Manning, P.A.

(57) ABSTRACT

A needle assembly for use with an autonomous ultrasound imaging system includes a needle having a proximal end and a distal end adapted to be inserted into a patient. The needle assembly also includes a needle transducer mounted to an exterior surface of the needle and is electrically coupled to a power source. The needle transducer is configured to receive data signals from the autonomous ultrasound imaging system which contain information relating to a plurality of ultrasound waves generated by an ultrasound probe of the autonomous ultrasound imaging system. The needle assembly further includes at least one processor configured to perform one or more operations, including but not limited to, generating a location signal for at least one portion of the needle based on the data signals from the autonomous ultrasound imaging system and modifying at least one characteristic of the location signal so as to improve visibility of the location signal on the display screen, wherein (Continued)

the modified location signal is displayed on a display screen during use of the needle assembly so as to locate the at least one portion of the needle.

14 Claims, 12 Drawing Sheets

(51) Int. Cl.
*A61B 8/00* (2006.01)
*A61B 34/20* (2016.01)
*A61B 17/34* (2006.01)
*A61B 90/00* (2016.01)

(52) U.S. Cl.
CPC ............ *A61B 8/4444* (2013.01); *A61B 34/20* (2016.02); *A61B 2034/2051* (2016.02); *A61B 2034/2063* (2016.02)

(58) Field of Classification Search
CPC .... A61B 2034/2051; A61B 2034/2063; A61B 17/3403; A61B 2017/3413; A61B 2090/3929; G05B 2219/1168; G01R 19/04; H03K 5/1532
See application file for complete search history.

(56) References Cited

U.S. PATENT DOCUMENTS

| | | | |
|---|---|---|---|
| 5,174,295 A | 12/1992 | Christian et al. | |
| 5,299,571 A | 4/1994 | Mastrototaro | |
| 5,344,435 A | 9/1994 | Turner et al. | |
| 5,354,220 A | 10/1994 | Ganguly et al. | |
| 5,357,955 A | 10/1994 | Wolf et al. | |
| 5,485,845 A | 1/1996 | Verdonk et al. | |
| 5,542,915 A | 8/1996 | Edwards et al. | |
| 5,829,439 A * | 11/1998 | Yokosawa ................. A61B 8/12 |
| | | | 600/461 |
| 5,954,649 A | 9/1999 | Chia et al. | |
| 5,989,276 A | 11/1999 | Houser et al. | |
| 6,165,164 A | 12/2000 | Hill et al. | |
| 6,554,801 B1 | 4/2003 | Steward et al. | |
| 6,582,368 B2 | 6/2003 | Holdaway et al. | |
| 6,862,468 B2 | 3/2005 | Smith | |
| 6,911,027 B1 | 6/2005 | Edwards et al. | |
| 7,699,829 B2 | 4/2010 | Harris et al. | |
| 7,713,200 B1 | 5/2010 | Sarvazyan et al. | |
| 8,147,414 B2 | 4/2012 | Abraham | |
| 8,167,805 B2 | 5/2012 | Emery et al. | |
| 8,282,565 B2 | 10/2012 | Mahapatra et al. | |
| 8,556,883 B2 | 10/2013 | Saleh | |
| 8,632,468 B2 | 1/2014 | Glossop et al. | |
| 9,179,971 B2 | 11/2015 | Kirschenman | |
| 9,301,690 B2 | 4/2016 | Razavi et al. | |
| 9,326,813 B2 | 5/2016 | Pike, Jr. et al. | |
| 9,445,746 B1 | 9/2016 | Elberse et al. | |
| 9,474,506 B2 | 10/2016 | Magnin et al. | |
| 9,855,021 B2 | 1/2018 | Abraham | |
| 9,972,082 B2 | 5/2018 | Holsing et al. | |
| 10,285,611 B1 * | 5/2019 | Harlev .................. A61B 5/316 |
| 2001/0047134 A1 | 11/2001 | Holdaway et al. | |
| 2004/0106869 A1 | 6/2004 | Tepper | |
| 2004/0162507 A1 | 8/2004 | Govari | |
| 2006/0135884 A1 | 6/2006 | Hack et al. | |
| 2006/0136133 A1 * | 6/2006 | Woerpel ................. G01V 1/40 |
| | | | 702/9 |
| 2007/0053513 A1 * | 3/2007 | Hoffberg ............... G06V 40/103 |
| | | | 380/201 |
| 2008/0114309 A1 | 5/2008 | Zuckerman | |
| 2008/0172119 A1 | 7/2008 | Yamasaki et al. | |
| 2009/0069808 A1 | 3/2009 | Pike, Jr. et al. | |
| 2009/0105597 A1 | 4/2009 | Abraham | |
| 2010/0010323 A1 | 1/2010 | Jobst | |
| 2010/0298705 A1 * | 11/2010 | Pelissier ............... A61B 8/4254 |
| | | | 600/443 |
| 2011/0166455 A1 | 7/2011 | Cully et al. | |
| 2012/0287750 A1 | 11/2012 | Deladi et al. | |
| 2013/0158459 A1 | 6/2013 | Goedje et al. | |
| 2013/0261467 A1 | 10/2013 | Dausch et al. | |
| 2014/0024911 A1 | 1/2014 | Harlev et al. | |
| 2014/0093234 A1 * | 4/2014 | Roberts ................. H04B 10/564 |
| | | | 398/79 |
| 2014/0121502 A1 | 5/2014 | Vignon et al. | |
| 2014/0171788 A1 | 6/2014 | Stigall | |
| 2014/0275810 A1 | 9/2014 | Keller et al. | |
| 2014/0316269 A1 | 10/2014 | Zhang et al. | |
| 2015/0201994 A1 | 7/2015 | Vetter | |
| 2015/0351645 A1 | 12/2015 | Hiltner | |
| 2016/0045184 A1 * | 2/2016 | Courtney ............... A61B 8/4494 |
| | | | 600/424 |
| 2016/0066987 A1 | 3/2016 | Budzelaar et al. | |
| 2016/0158509 A1 | 6/2016 | Wedan et al. | |
| 2017/0000980 A1 | 1/2017 | Potosky | |
| 2017/0020422 A1 | 1/2017 | Bigelow et al. | |
| 2017/0020562 A1 | 1/2017 | Erkamp et al. | |
| 2017/0027605 A1 | 2/2017 | Erkamp et al. | |
| 2017/0033474 A1 | 2/2017 | Erkamp et al. | |
| 2017/0172544 A1 | 6/2017 | Erkamp et al. | |
| 2017/0172618 A1 * | 6/2017 | Erkamp ................ A61B 8/4494 |
| 2017/0196591 A1 | 7/2017 | Long, Jr. et al. | |
| 2018/0036513 A1 | 2/2018 | Cruz, Jr. et al. | |
| 2018/0064415 A1 | 3/2018 | Zhai et al. | |
| 2018/0078170 A1 | 3/2018 | Panescu et al. | |
| 2018/0085519 A1 | 3/2018 | McCaffrey et al. | |
| 2018/0116629 A1 | 5/2018 | Boctor et al. | |
| 2018/0132754 A1 | 5/2018 | Kusumoto | |
| 2018/0132945 A1 | 5/2018 | Fazzi | |
| 2018/0146981 A1 | 5/2018 | De Wijs et al. | |
| 2019/0201110 A1 * | 7/2019 | Kuenen ............... G01S 15/8993 |

FOREIGN PATENT DOCUMENTS

| | | |
|---|---|---|
| GB | 2 423 255 A | 8/2006 |
| KR | 20120061340 A | 6/2012 |
| WO | WO 89/09633 | 10/1989 |
| WO | WO 2014/139005 A1 | 9/2014 |
| WO | WO 2018/116114 A1 | 6/2018 |

OTHER PUBLICATIONS

International Search Report and Written Opinion for PCT/US2019/067055, dated Apr. 17, 2020, 12 pages.
Duan et al., "Synthesis of Ca—P nanoparticles and fabrication of Ca—P/PHBV nanocomposite microspheres for bone tissue engineering applications", Applied Surface Science, Elsevier, 2008, pp. 529-533.

* cited by examiner

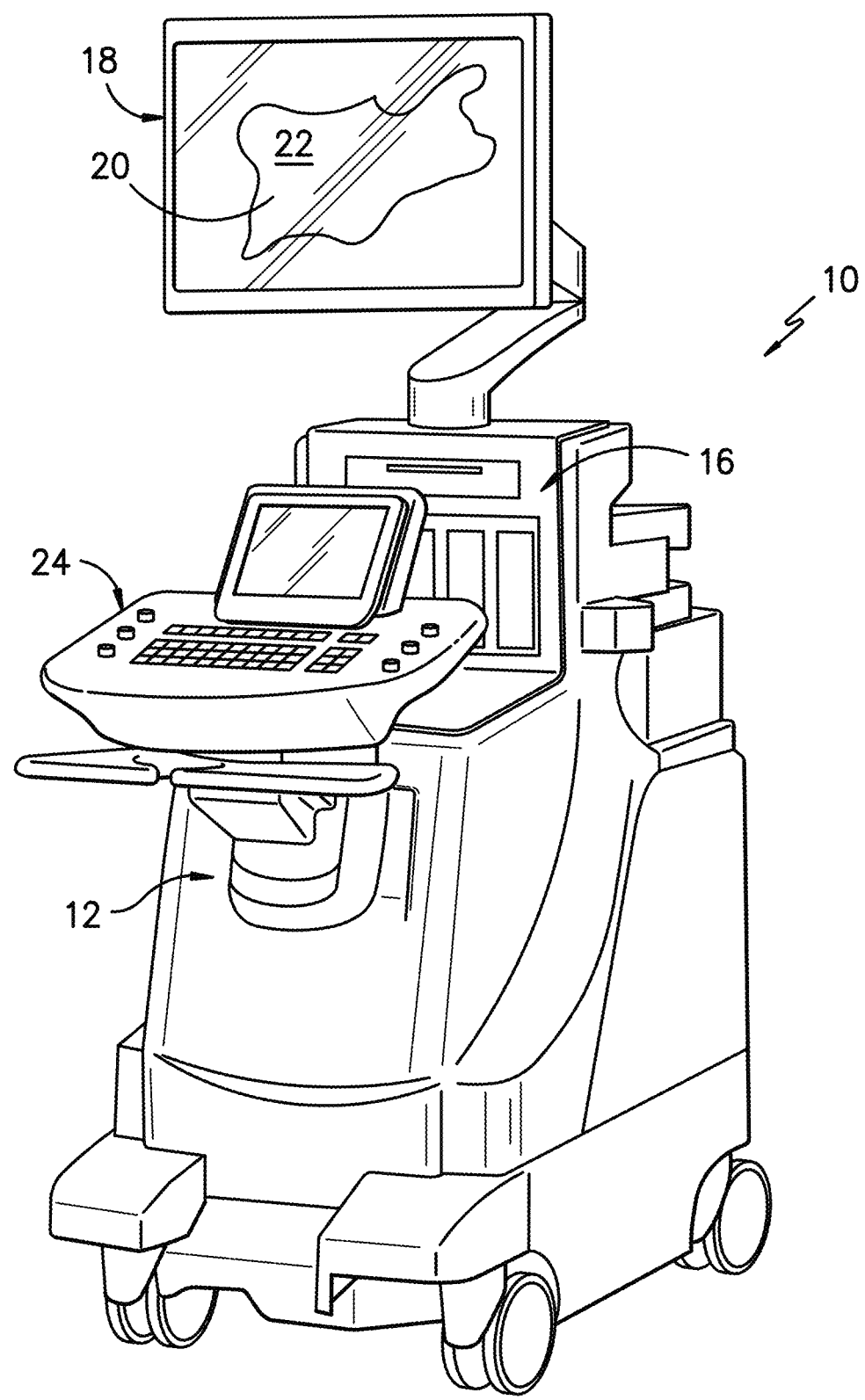
FIG. -1-

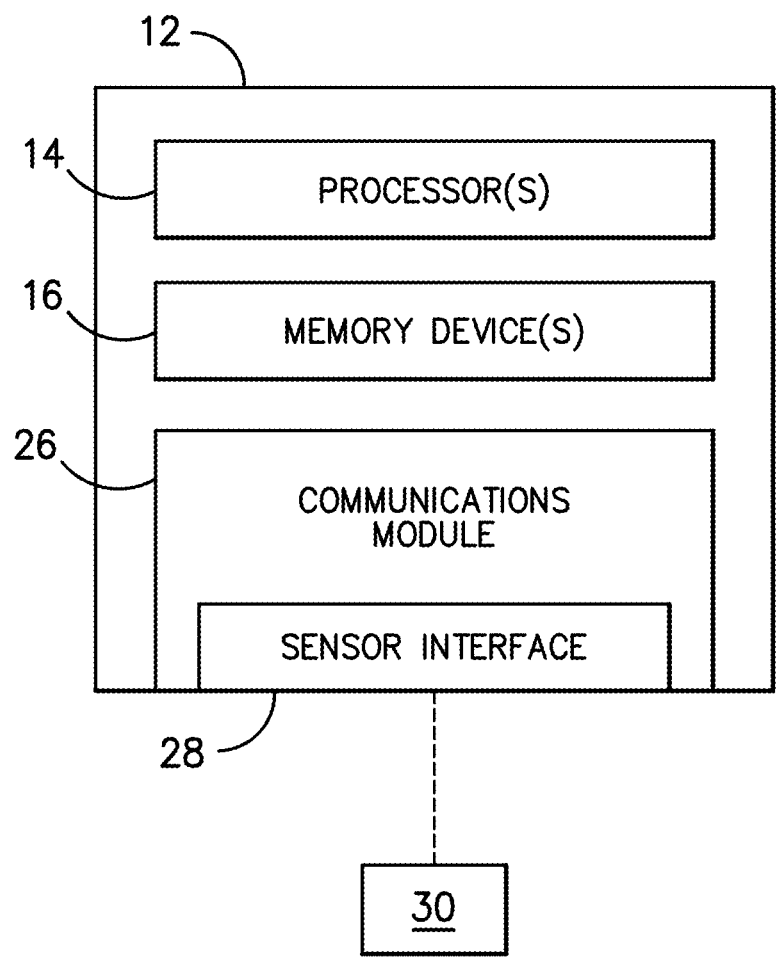
FIG. -2-

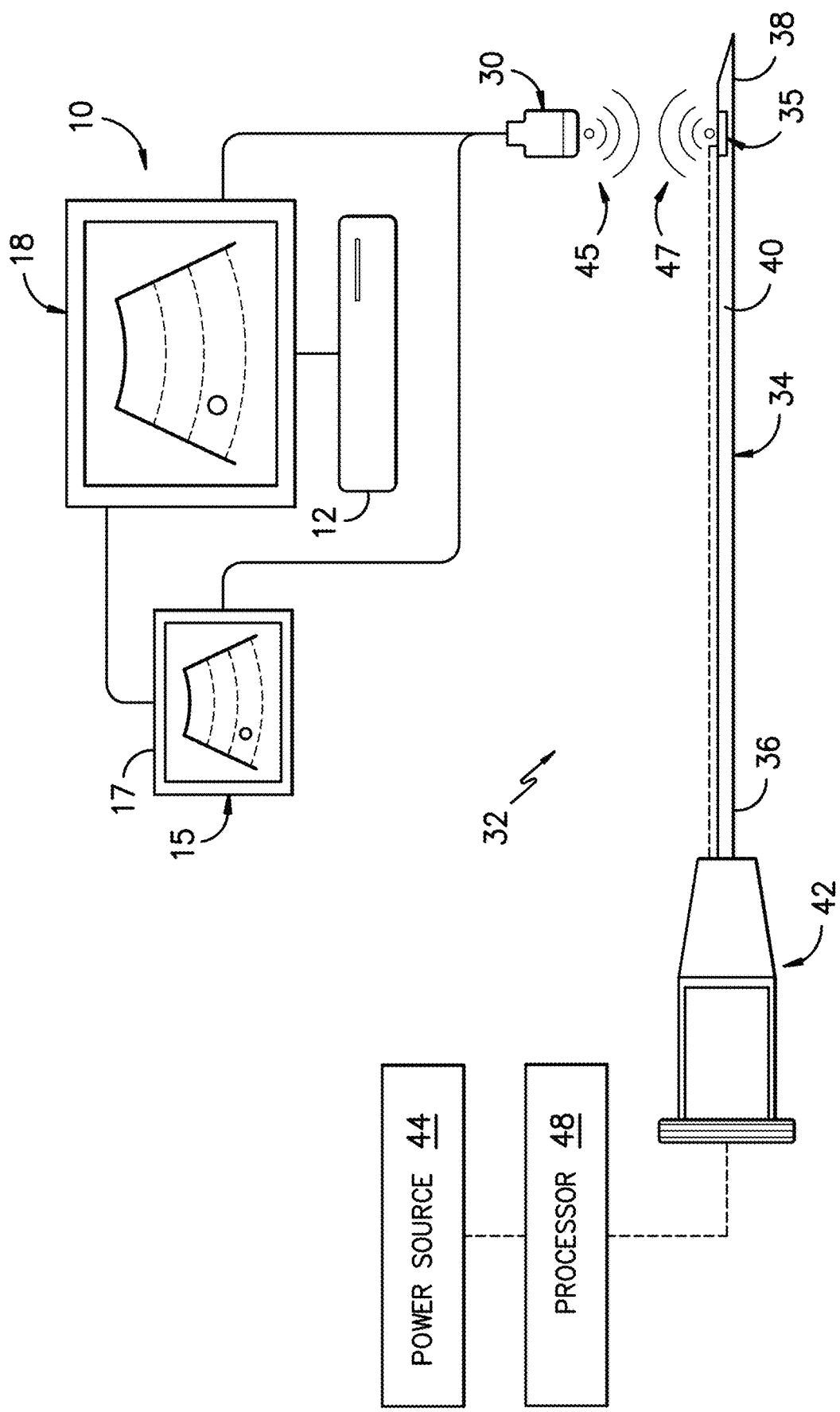
FIG. -3-

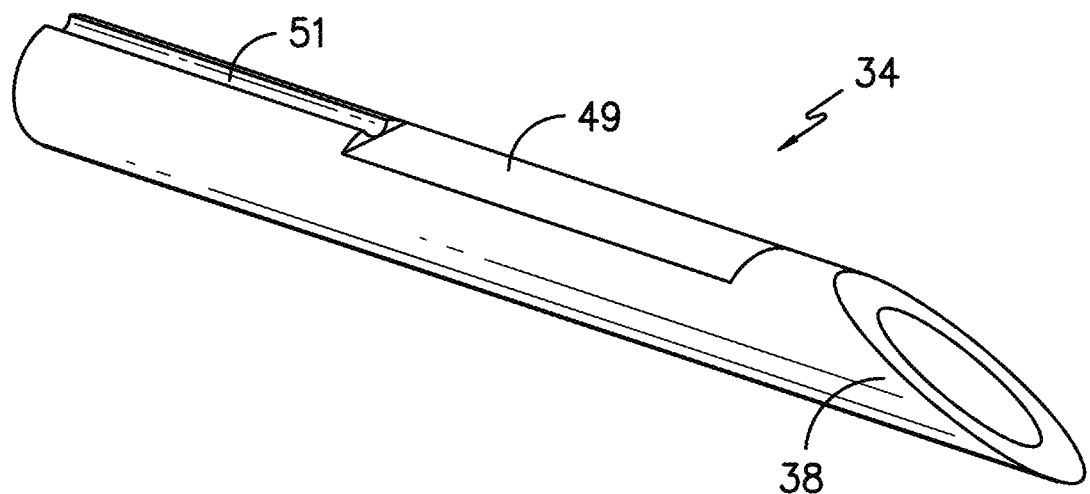
FIG. -4-
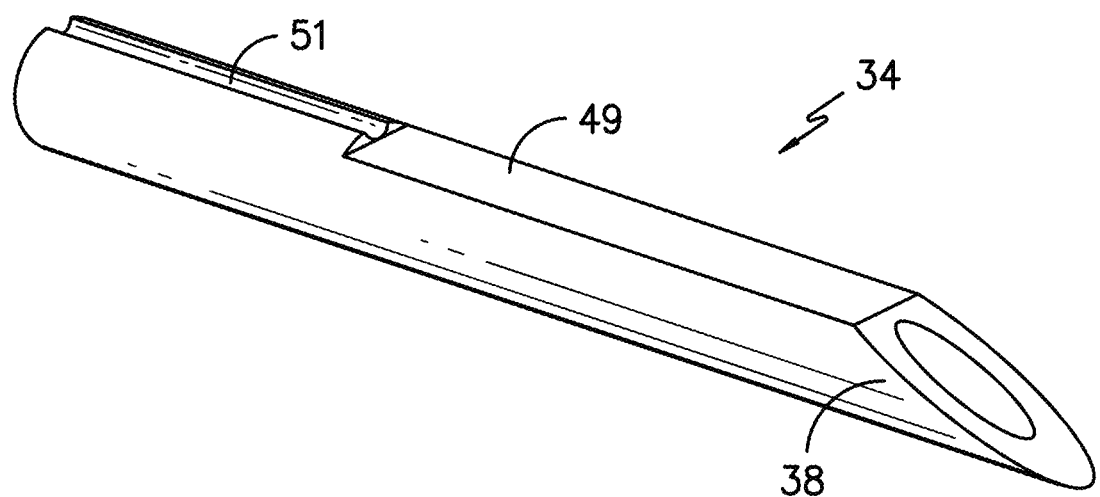
FIG. -5-

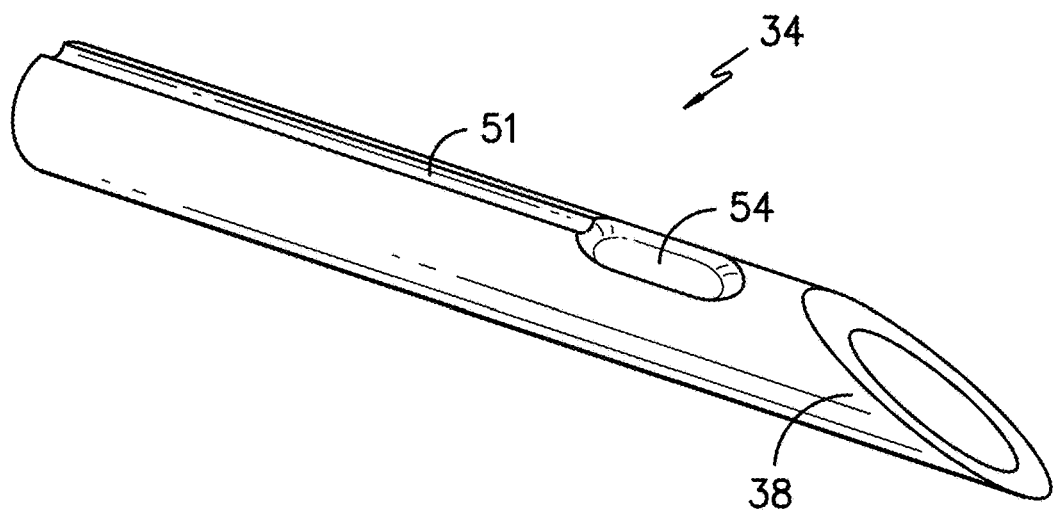
FIG. -6-
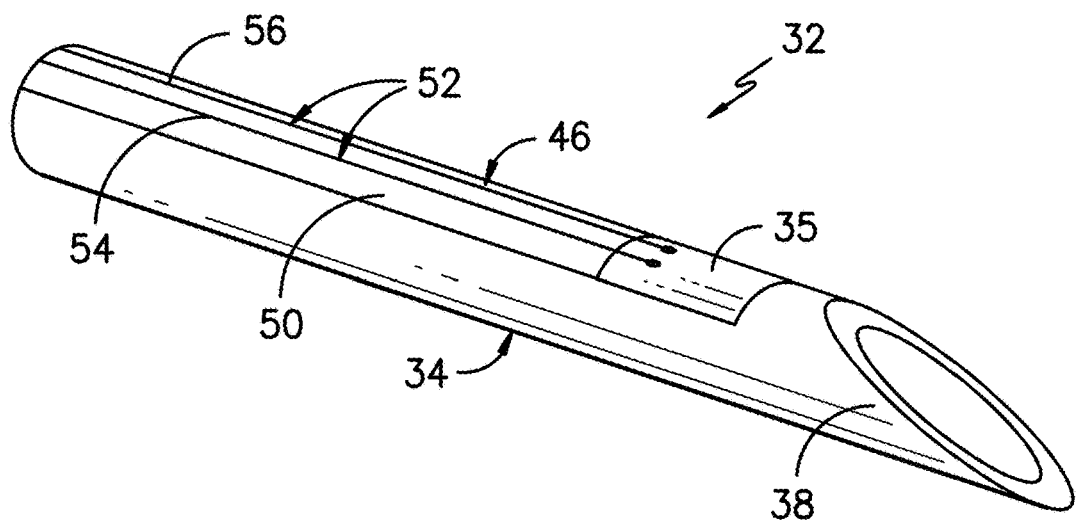
FIG. -7-
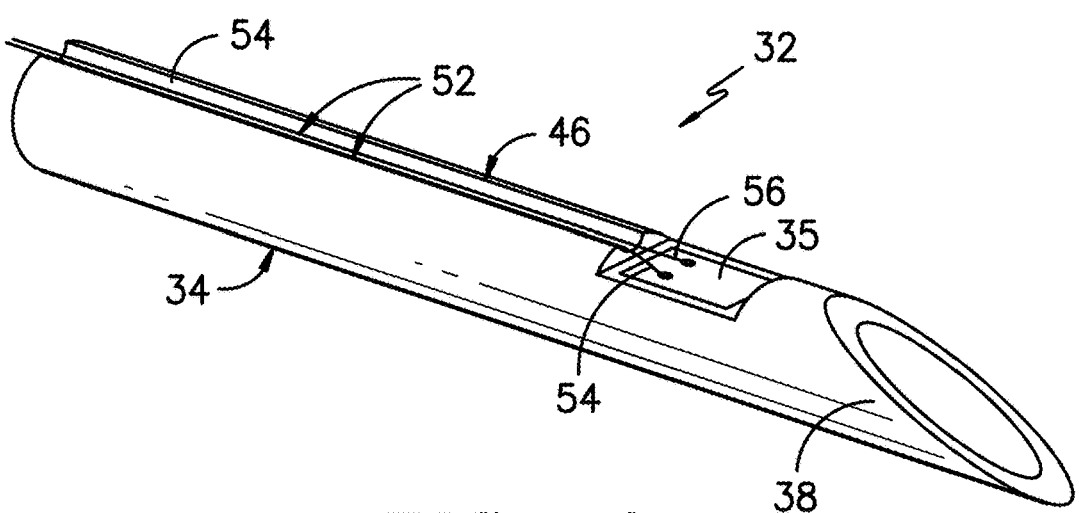
FIG. -8-

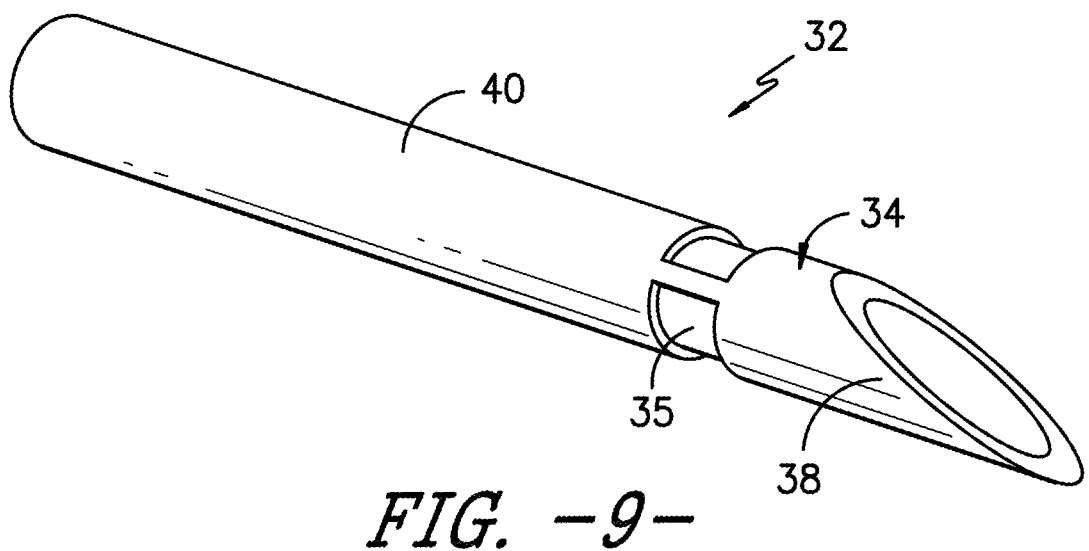
FIG. -9-
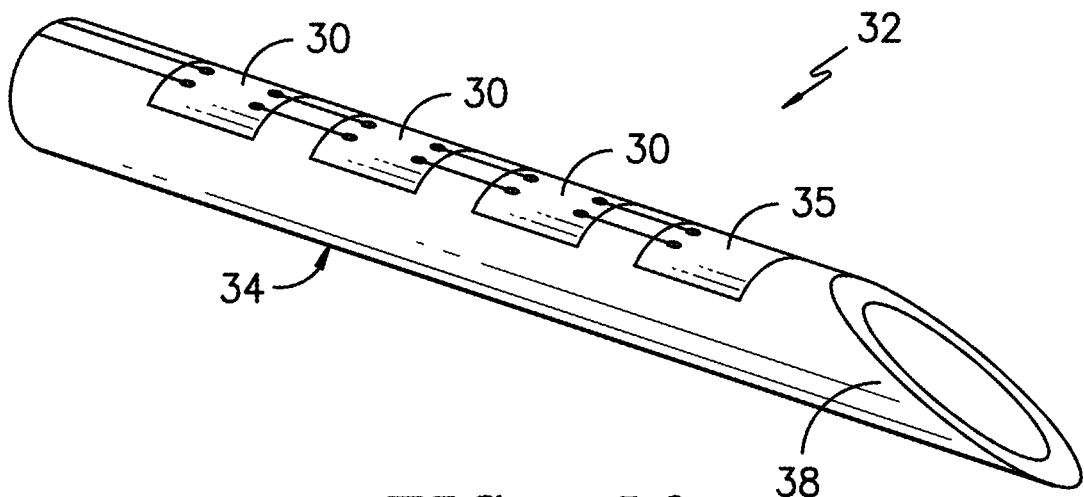
FIG. -10-
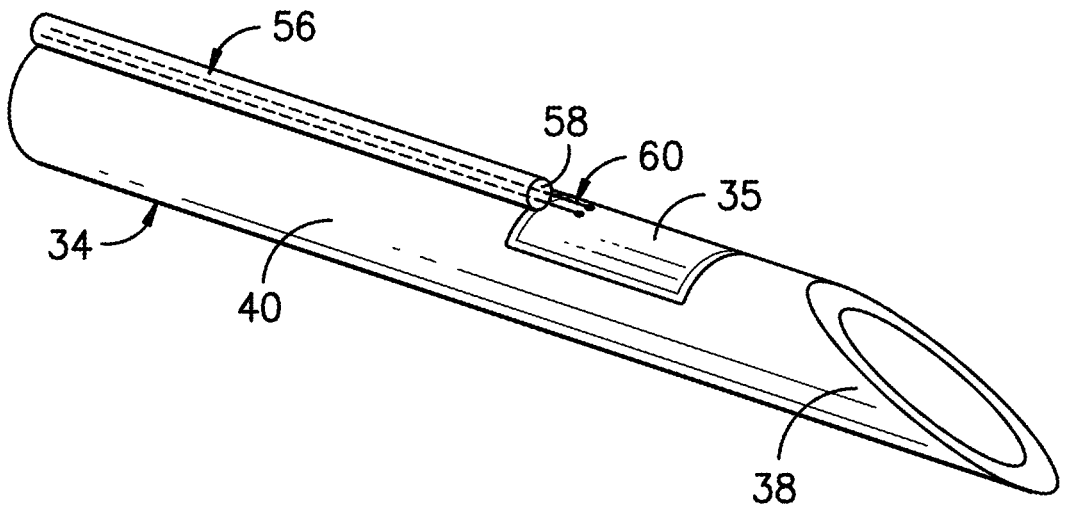
FIG. -11-

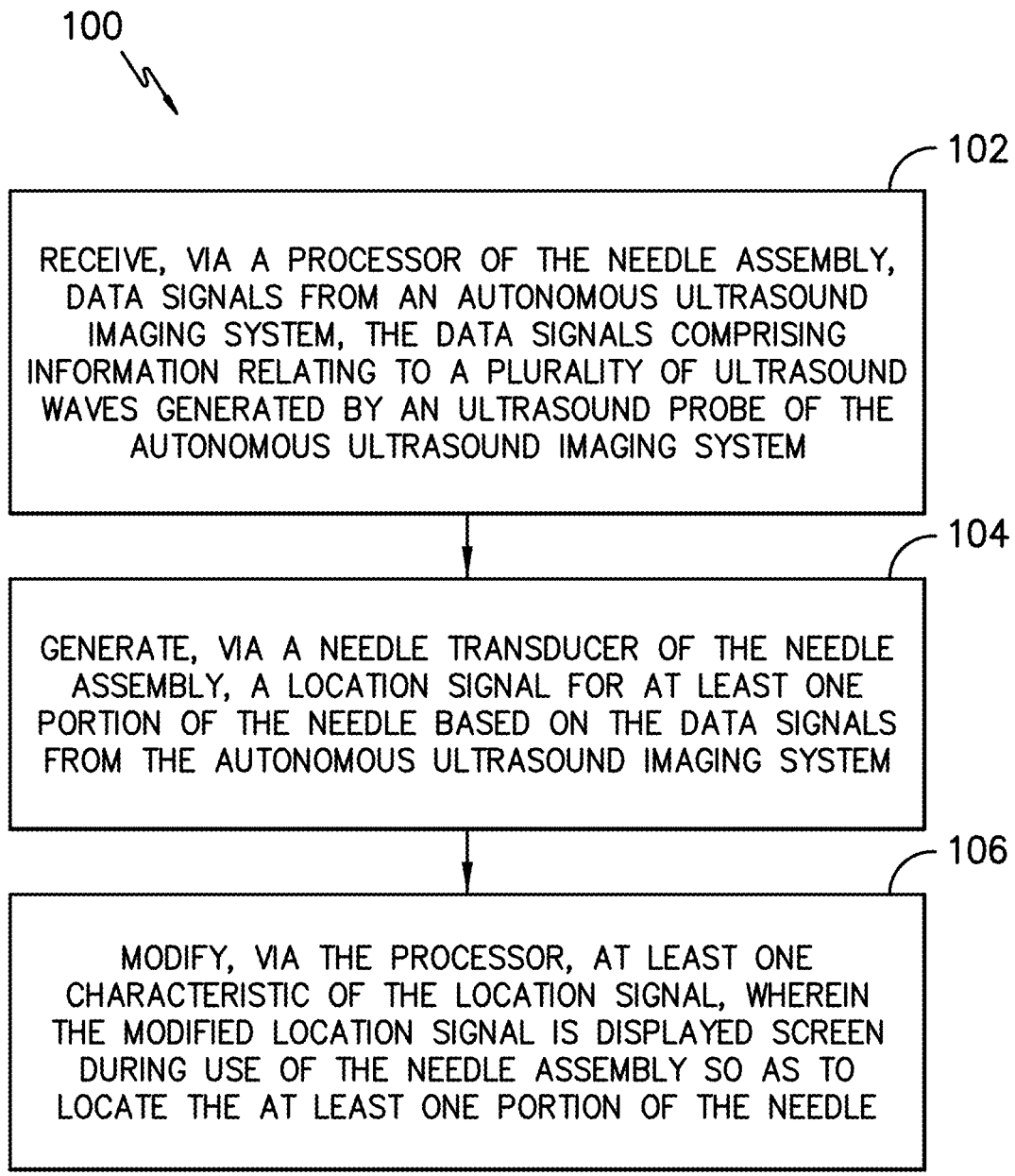
FIG. -12-

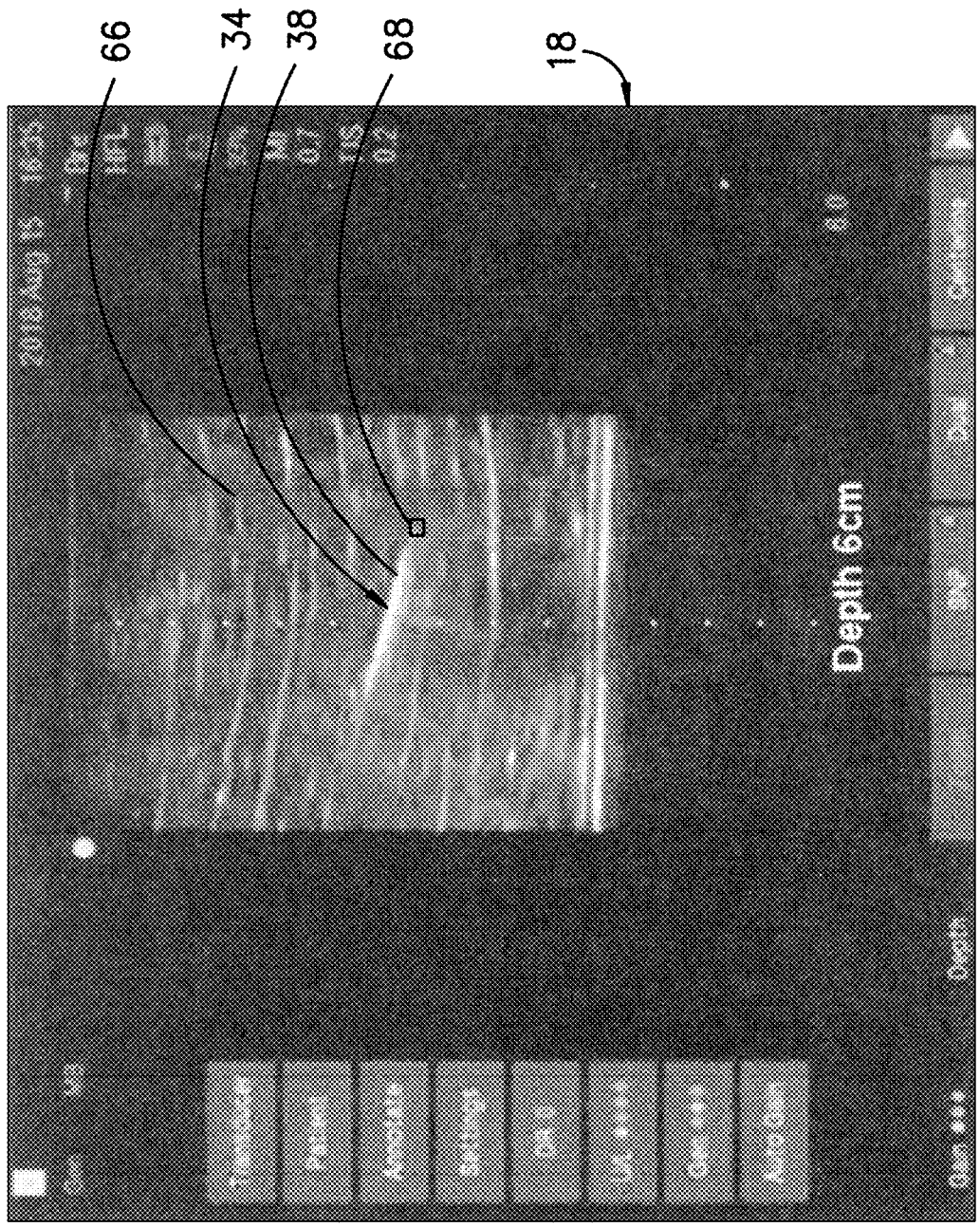
FIG. -13-

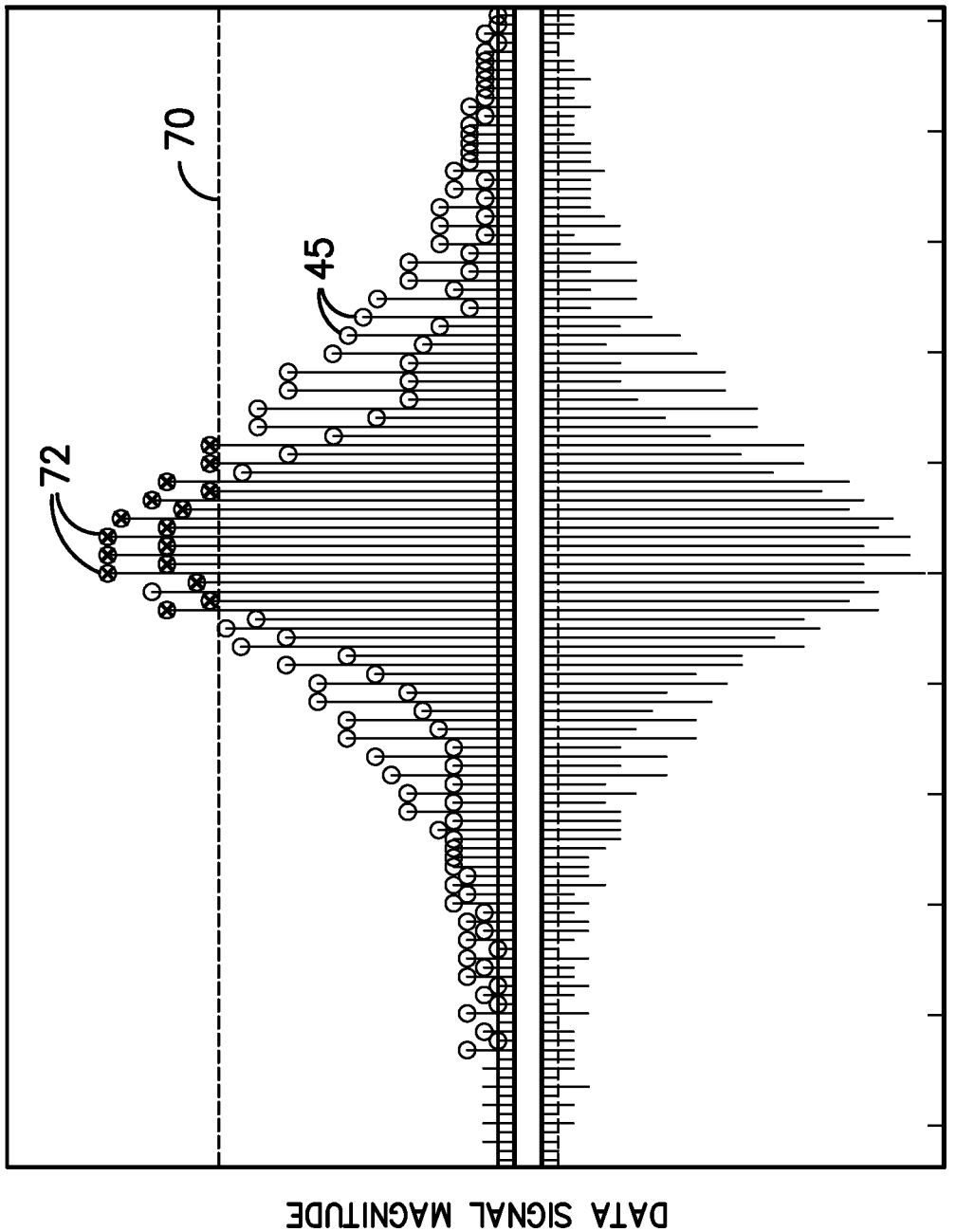
FIG. -14-

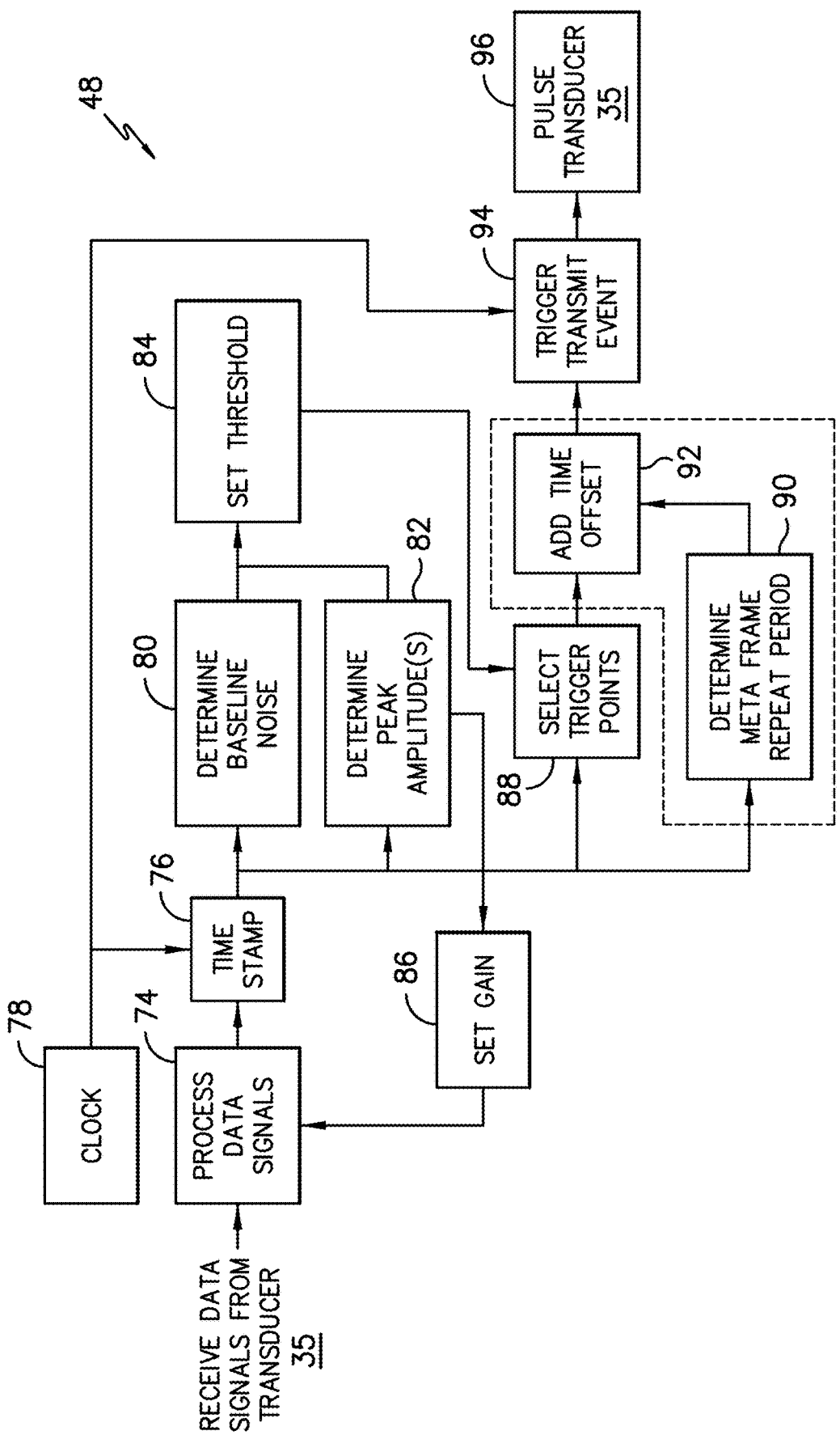
FIG. -15-

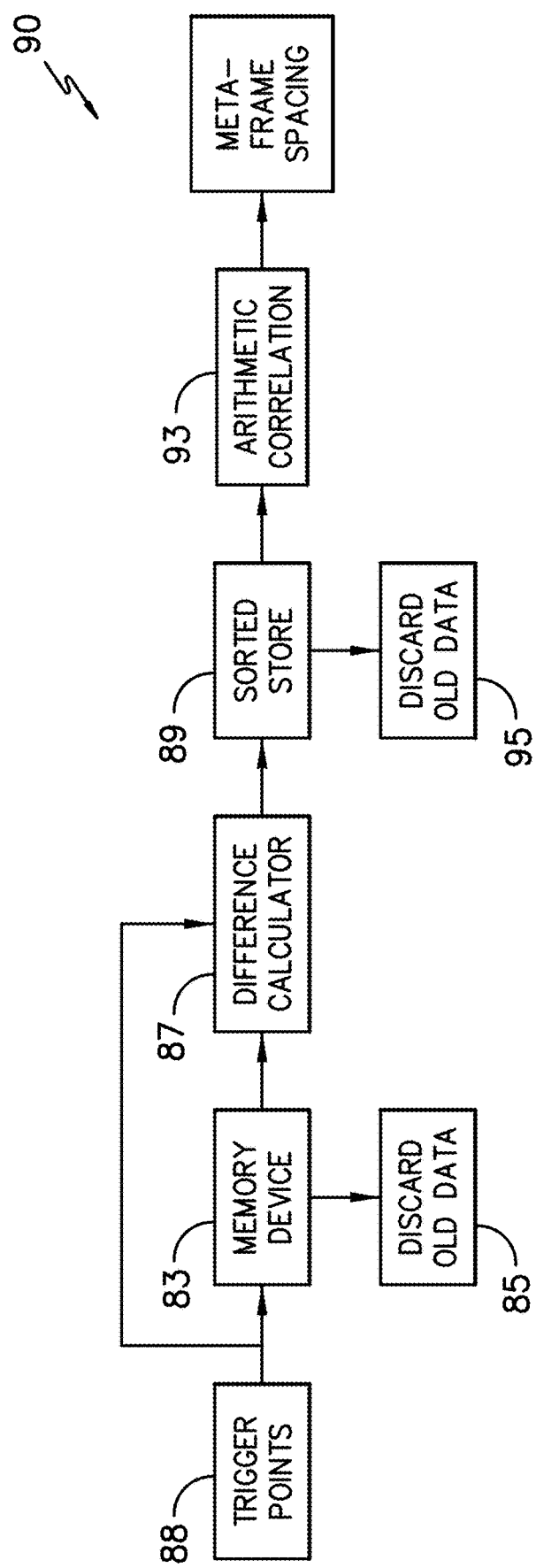
FIG. -16-

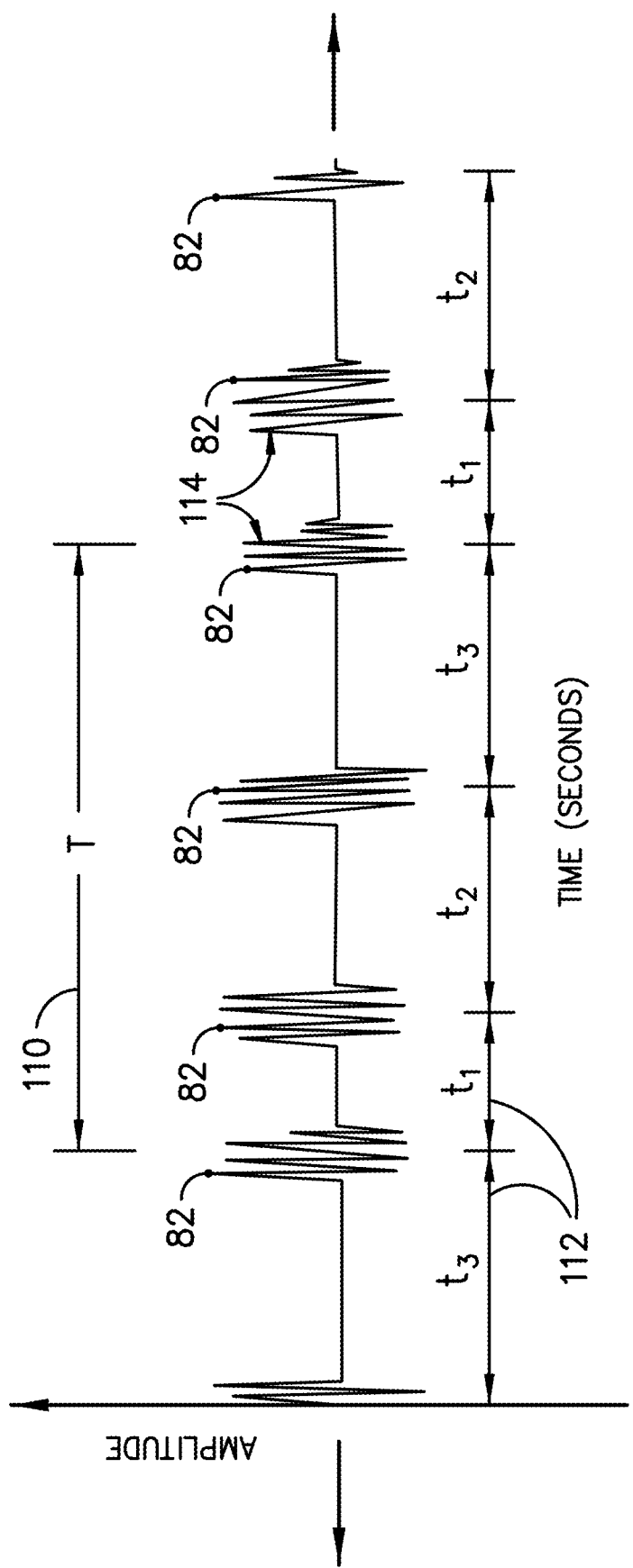
FIG. -17-

METHODS FOR NEEDLE IDENTIFICATION ON AN ULTRASOUND DISPLAY SCREEN BY DETERMINING A META-FRAME RATE OF THE DATA SIGNALS

FIELD

The present invention relates generally to needle assemblies for use in medical procedures, and more particularly, to a method for identifying a portion of a needle of a needle assembly (such as the distal tip thereof) on a display screen.

BACKGROUND

Detection of anatomical objects using medical imaging is an essential step for many medical procedures, such as regional anesthesia nerve blocks, and is becoming the standard in clinical practice to support diagnosis, patient stratification, therapy planning, intervention, and/or follow-up. Various systems based on traditional approaches exist for anatomical detection and tracking in medical images, such as computed tomography (CT), magnetic resonance (MR), ultrasound, and fluoroscopic images.

For example, ultrasound imaging systems utilize sound waves with frequencies higher than the upper audible limit of human hearing. Further, ultrasound imaging systems are widely used in medicine to perform both diagnosis and therapeutic procedures. In such procedures, sonographers perform scans of a patient using a hand-held probe or transducer that is placed directly on and moved over the patient.

Certain ultrasound systems may be used in combination with needles having active (i.e. electrically-powered) transducers, which require an electrical connection to a power source. Such needles, however, can often be difficult to locate on an ultrasound display screen. Particularly, for anesthesiologists, it is often difficult to locate the needle tip on the ultrasound display during peripheral nerve block (PNB) procedures (both single shots and continuous).

Accordingly, the present disclosure is directed to a method for identifying a portion of a needle of a needle assembly, such as the distal tip, on a display screen of an autonomous ultrasound imaging system and/or an add-on system to the autonomous ultrasound imaging system that addresses the aforementioned issues.

SUMMARY

Objects and advantages of the invention will be set forth in part in the following description, or may be obvious from the description, or may be learned through practice of the invention.

In one aspect, the present invention is directed to a method for identifying a needle of a needle assembly on a display screen. The method includes receiving, via a needle assembly of the needle assembly, data signals from the autonomous ultrasound imaging system. The data signals include information relating to a plurality of ultrasound waves generated by an ultrasound probe of the autonomous ultrasound imaging system. The method also includes generating, via the needle transducer of the needle assembly, a location signal for at least one portion of the needle based on the data signals from the autonomous ultrasound imaging system. Further, the method includes modifying, via a processor of the needle assembly, at least one characteristic of the location signal so as to improve visibility of the location signal on the display screen, wherein the modified location signal is displayed on a display screen during use of the needle assembly so as to locate the at least one portion of the needle.

In one embodiment, generating the location signal for the portion of the needle based on the data signals from the autonomous ultrasound imaging system may include determining, via the processor the needle assembly, a threshold for the data signals and identifying, via the processor, a plurality of peak amplitudes within the data signals based on when the data signals exceed the threshold. In such embodiments, determining the threshold for the data signals may include determining a baseline noise for the data signals and subsequently determining the threshold for the data signals by eliminating the baseline noise therefrom.

In another embodiment, generating the location signal for the portion of the needle based on the data signals from the autonomous ultrasound imaging system may further include determining a meta-frame repeat period of the data signals, determining a time offset for the data signals based on the meta-frame repeat period, anticipating a future frame rate of the autonomous ultrasound imaging system based on the time offset, and signaling to the needle transducer of the needle assembly to flash so as to display the location signal at the at least one portion of the needle on the display screen in anticipation of the future frame rate.

In such embodiments, determining the meta-frame repeat period of the data signals may include receiving the plurality of peak amplitudes, storing the plurality of peak amplitudes, determining a time frame between the stored plurality of peak amplitudes, maintaining a record of the time frames between each of the plurality of peaks, applying an arithmetic correlation to the record of the time frames, and/or determining the meta-frame repeat period of the autonomous ultrasound imaging system based on the record of the time frames.

In further embodiments, the method may include pulsing the location signal at a known pulse rate using the known pulse rate to extract the location signal from ultrasound signal noise. In additional embodiments, modifying the characteristic(s) of the location signal may include collecting multiple pulsed location signals and processing the collected pulsed location signals via at least one of filtering the collected pulsed location signals, transforming one or more of the collected pulsed location signals, or removing outliers from the collected pulsed location signals. In addition, in one embodiment, the characteristic(s) of the location signal may include, for example, color, shape, size, brightness, intensity, rate of flashing, and/or echogenicity.

Thus, in particular embodiments, the location signal may include a periodically flashing marker and/or a reflective marker coinciding with the at least one portion of the needle. For example, in one embodiment, the portion of the needle may include a distal end of the needle.

In another aspect, the present disclosure is directed to a needle assembly for use with an autonomous ultrasound imaging system. The needle assembly includes a needle having a proximal end and a distal end adapted to be inserted into a patient. The needle assembly also includes a needle transducer mounted to an exterior surface of the needle and is electrically coupled to a power source. The needle transducer is configured to receive data signals from the autonomous ultrasound imaging system which contain information relating to a plurality of ultrasound waves generated by an ultrasound probe of the autonomous ultrasound imaging system. The needle assembly further includes at least one processor configured to perform one or more operations, including but not limited to, generating a location signal for at least one portion of the needle based on the data signals from the autonomous ultrasound imaging system and modifying at least one characteristic of the location signal so as to improve visibility of the location signal on the display screen, wherein the modified location signal is displayed on a display screen during use of the needle assembly so as to locate the at least one portion of the needle. It should be further understood that the needle assembly may include any of the additional features and/or steps described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an imaging system according to the present disclosure;

FIG. 2 illustrates a block diagram one of embodiment of a controller of an imaging system according to the present disclosure;

FIG. 3 illustrates a schematic diagram of one embodiment of a needle assembly according to the present disclosure, particularly illustrating the needle assembly communicating with an autonomous ultrasound imaging system and/or an add-on system of the autonomous ultrasound imaging system;

FIG. 4 illustrates a perspective view of a portion of one embodiment of a distal end of a needle assembly according to the present disclosure, particularly illustrating the location for a transducer and corresponding wire, wherein the location for the transducer is an embedded flat portion within the needle wall;

FIG. 5 illustrates a perspective view of a portion of another embodiment of a distal end of a needle assembly according to the present disclosure, particularly illustrating the location for a transducer and corresponding wire, wherein the location for the transducer is a flat portion that extends to the distal end of the needle;

FIG. 6 illustrates a perspective view of a portion of still another embodiment of a distal end of a needle assembly according to the present disclosure, particularly illustrating the location for a transducer and corresponding wire, wherein the location for the transducer is a recess within the wall of the needle;

FIG. 7 illustrates a perspective view of a portion of yet another embodiment of a distal end of needle assembly according to the present disclosure, particularly illustrating a flexible printed circuit board mounted onto an exterior surface of the needle;

FIG. 8 illustrates a perspective view of a portion of another embodiment of a distal end of needle assembly according to the present disclosure, particularly illustrating a flexible printed circuit board mounted with a recess of the needle so as to electrically connect a needle transducer at the distal end to a power source;

FIG. 9 illustrates a perspective view of a portion of still another embodiment of a distal end of a needle assembly according to the present disclosure, particularly illustrating a plurality of needle transducers radially spaced around a circumference of the needle;

FIG. 10 illustrates a perspective view of a portion of yet another embodiment of a distal end of needle assembly according to the present disclosure, particularly illustrating a plurality of needle transducers mounted along a length of the needle;

FIG. 11 illustrates a perspective view of another embodiment of a distal end of a needle assembly according to the present disclosure, particularly illustrating a conduit assembly mounted onto an exterior surface of the needle so as to electrically connect a transducer at the distal end to a power source;

FIG. 12 illustrates a flow chart of one embodiment of a method for identifying a needle of a needle assembly on a display screen according to the present disclosure;

FIG. 13 illustrates a sample image from a display screen according to the present disclosure, particularly illustrating a location marker generated by a needle assembly reflected thereon;

FIG. 14 illustrates a graph of one embodiment of data signals received from the ultrasound imaging system by a needle assembly according to the present disclosure, particularly illustrating a predetermined threshold set with respect to the data signals as a function of a signal-to-noise ratio of the data signals FIG. 15 illustrates a flow diagram of one embodiment of a system for identifying a needle of a needle assembly on a display screen according to the present disclosure;

FIG. 16 illustrates a flow diagram of one embodiment for determining a meta-frame repeat period of an autonomous ultrasound imaging system according to the present disclosure; and FIG. 17 illustrates a graph of amplitude (y-axis) versus time (x-axis) that includes one embodiment of a plurality of ultrasound bursts according to the present disclosure.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Referring now to the drawings, FIGS. 1-3 illustrate a medical imaging system 10 for scanning, identifying, and navigating anatomical objects of a patient according to the present disclosure. As used herein, the anatomical object(s) 22 and surrounding tissue described herein may include any anatomical structure and/or surrounding tissue of a patient. For example, in one embodiment, the anatomical object(s) 22 may include one or more nerves or nerve bundles. More specifically, in another embodiment, the anatomical object(s) 22 may include an interscalene brachial plexus of the patient, which generally corresponds to the network of nerves running from the spine, formed by the anterior rami of the lower four cervical nerves and first thoracic nerve. As such, the surrounding tissue of the brachial plexus generally corresponds to the sternocleidomastoid muscle, the middle scalene muscle, the anterior scalene muscle, and/or similar.

It should be understood, however, that the system of the present disclosure may be further used for any variety of medical procedures involving any anatomical structure in addition to those relating to the brachial plexus. For example, the anatomical object(s) 22 may include upper and lower extremities, as well as compartment blocks. More specifically, in such embodiments, the anatomical object(s) 22 of the upper extremities may include interscalene muscle, supraclavicular muscle, infraclavicular muscle, and/or axillary muscle nerve blocks, which all block the brachial plexus (a bundle of nerves to the upper extremity), but at different locations. Further, the anatomical object(s) 22 of the lower extremities may include the lumbar plexus, the Iliac fascia, the femoral nerve, the sciatic nerve, the adductor canal, the popliteal, the saphenous, and/or similar. In addition, the anatomical object(s) 22 of the compartment blocks may include the intercostal space, transversus abdominis plane, and thoracic paravertebral space, and/or similar.

In addition, as shown, the imaging system 10 may correspond to an autonomous ultrasound imaging system or any other suitable imaging system that can benefit from the present technology. In addition, as shown, an additional add-on system 15 may also be used in conjunction with the autonomous ultrasound imaging system, which will be discussed in more detail herein. Further, as shown, the imaging system 10 may generally include a controller 12 having one or more processor(s) 14 and associated memory device(s) 16 configured to perform a variety of computer-implemented functions (e.g., performing the methods and the like and storing relevant data as disclosed herein), as well as a display screen 18 configured to display an image 20 of an anatomical object 22 or the surrounding tissue to an operator. In addition, the imaging system 10 may include a user interface 24, such as a computer and/or keyboard, configured to assist a user in generating and/or manipulating the display screen 18. Further, as shown, the add-on system 15 may also include an additional display screen 17.

Additionally, as shown in FIG. 2, the processor(s) 14 may also include a communications module 26 to facilitate communications between the processor(s) 14 and the various components of the imaging system 10, e.g. any of the components of FIG. 1. Further, the communications module 26 may include a sensor interface 28 (e.g., one or more analog-to-digital converters) to permit signals transmitted from one or more probes (e.g. such as an ultrasound probe 30 and/or the needle transducer 35) to be converted into signals that can be understood and processed by the processor(s) 14. It should be appreciated that the various probes/sensors described herein may be communicatively coupled to the communications module 26 of the controller 12 using any suitable means. For example, as shown in FIG. 2, the ultrasound probe 30 may be coupled to the sensor interface 28 via a wired connection. However, in other embodiments, the ultrasound probe 30 may be coupled to the sensor interface 28 via a wireless connection, such as by using any suitable wireless communications protocol known in the art. As such, the processor(s) 14 may be configured to receive one or more sensor signals from the ultrasound probe 30.

Referring now to FIG. 3, a side view of one embodiment of a needle assembly 32 according to the present disclosure that can be used in combination with the autonomous ultrasound imaging system 10 is illustrated. More specifically, as shown, the needle assembly 32 includes a needle 34 having a proximal end 36 and a distal end 38 adapted to be inserted into a patient and a needle transducer 35, which is mounted to an exterior surface 40 of the needle 34, e.g. at the distal end 38 thereof. However, in additional embodiments, it should be understood that the needle transducer 35 may be located at any location along the needle 4. In addition, as shown, the needle assembly 32 may also include at least one processor 48 configured to process information relating to the various components of the needle assembly 32. For example, as shown, the processor 48 may be configured to receive, at least, data signals 45 from the ultrasound probe 30 i.e. relating to ultrasound waves generated by the ultrasound probe 30 of the autonomous ultrasound imaging system 10. Further, as shown, the processor 48 may be configured to send, at least, data signals 47 from the needle transducer 35 i.e. relating to a location thereof. Moreover, the needle 34 may also include a needle hub 42 at its proximal end 36. Moreover, the needle transducer 35 may be coupled to a power source 44, e.g. through the needle hub 42, that provides electrical power to the needle transducer 35.

As used herein, the term "processor" refers not only to integrated circuits referred to in the art as being included in a computer, but also refers to a controller, a microcontroller, a microcomputer, a programmable logic controller (PLC), a field-programmable gate array (FPGA), an Application-Specific Integrated Circuit (ASIC), and other programmable circuits. As such, the processors 14, 45 described herein are also configured to compute advanced control algorithms and communicate to a variety of Ethernet or serial-based protocols (Modbus, OPC, CAN, etc.). Furthermore, in certain embodiments, the processors 14, 45 may communicate with a server through the Internet for cloud computing in order to reduce the computation time and burden on the local device.

Additionally, the memory device(s) described herein may generally include memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) may generally be configured to store suitable computer-readable instructions that, when implemented by the processors 14, 45, configure the processors 14, 45 to perform the various functions as described herein.

In addition, the needle transducer 35 may be any suitable transducer now known or later developed in the art. For example, in one embodiment, the transducer 35 may be a piezoelectric (PZT) transducer. Alternatively, the transducer 35 may be a capacitive micromachined ultrasonic transducer (CMUT). In yet another embodiment, the transducer(s) 30 may also include Polydimethylsiloxane (PDMS) transducers and/or photoacoustic transducers.

Referring now to FIGS. 4-6, perspective views of different embodiments of the needle 34 of the needle assembly 32 are illustrated. More specifically, FIG. 4 illustrates a perspective view of one embodiment of the distal end 38 of the needle 34 according to the present disclosure, particularly illustrating the location for the needle transducer 35 on a flat portion 49 of the needle 34 and the corresponding wire(s) within a longitudinal groove 51 of the needle 34. Alternatively, FIG. 5 illustrates a perspective view of one embodiment of the distal end 38 of the needle 34 according to the present disclosure, particularly illustrating the location for the needle transducer 35 atop a flat portion that extends to the distal end 38 of the needle 34 and the corresponding wire(s) also within a longitudinal groove 51. In still another embodiment, FIG. 6 illustrates a perspective view of yet another embodiment of the distal end 38 of the needle 34 according to the present disclosure, particularly illustrating the location for the needle transducer 35 within the recess 54 of the needle 34 and the corresponding wire(s) also within a longitudinal groove 51.

Referring now to FIGS. 7-11, various example needle assemblies 32 are provided according the present disclosure. FIG. 7 illustrates a detailed view of one embodiment of the needle assembly 32 according to the present disclosure, particularly illustrating a flexible printed circuit board 46 being utilized to electrically connect the power source 44 and the needle transducer 35 is illustrated. FIG. 8 illustrates a perspective view of a portion of another embodiment of the distal end 38 of the needle 34 according to the present disclosure, particularly illustrating the flexible printed circuit board 46 mounted with the recess 54 of the needle 34 so as to electrically connect the needle transducer 35 to the power source 44. FIG. 9 illustrates a perspective view of a portion of still another embodiment of the distal end 38 of the needle 34 according to the present disclosure, particularly illustrating a plurality of needle transducers 30 radially spaced around a circumference of the needle 34. FIG. 10 illustrates a perspective view of a portion of yet another embodiment of the distal end 38 of the needle 34 according to the present disclosure, particularly illustrating a plurality of needle transducers 30 mounted along a length of the needle 34. FIG. 11 illustrates yet another perspective view of one embodiment of the distal end 38 of the needle 34 according to the present disclosure, particularly illustrating a conduit assembly 56 for receiving the associated wires for connecting the needle transducer 35 to the power source 44.

More specifically, as shown in FIGS. 7 and 8, the flexible printed circuit board 46 may be mounted on the exterior surface 40 of the needle 34 and may extend from the proximal end 36 to the distal end 38. Thus, as shown, the flexible printed circuit board 46 is configured to electrically connect the needle transducer 35 to the power source 44. In one embodiment, the flexible printed circuit board 46 may include, for example, a flexible base 50 having a plurality of conductive tracks 52 or traces printed thereon. As such, the flexible base 50 can easily flex with the shape of the needle 34 so as to be effectively mounted onto the exterior surface 40 of needle 34. For example, in certain embodiments, the conductive tracks 52 may be printed onto the flexible base 50 via screen printing, flexography, gravure printing, offset lithography, inkjet printing, additive manufacturing (e.g. 3D printing) and/or any other suitable printing process. In another embodiment, the flexible base 50 may be omitted.

In several embodiments, the various components of the flexible printed circuit board 46 may be printed on the exterior surface 40 of needle 34 via the additive manufacturing process. In such embodiments, the additive manufacturing process may include, for example, directed energy deposition, direct laser deposition, or any other suitable additive manufacturing process. By using additive manufacturing, the various components of the flexible printed circuit board 46 can be printed onto the needle 34 in thin layers so as not to disturb the overall efficacy of the needle 34 in puncturing the necessary tissue of the patient. For example, in one embodiment, the conductive tracks 52 may have a predetermined thickness ranging from about 0.01 millimeters (mm) to about 0.05 mm. As used herein, terms of degree, such as "about," are meant to encompass a range of +/−10% from the value set forth. In addition, in such embodiments, the conductive traces 52 may be narrow, such as from about 0.10 millimeter (mm) up to about 0.25 mm. Further, in certain embodiments, ground planes can be used to enclose the signal trace to achieve better noise immunity.

In addition to being mounted at the distal end 38 of the needle 34, it should also be understood that the needle transducer 35 may also be mounted at any suitable location on the needle 34. Further, as shown in FIGS. 3-8, the needle transducer 35 may be mounted on one side of the needle 34. In such embodiments, during operation, the user of the needle assembly 32 must orient the needle transducer 35 towards the ultrasound probe 30 of the ultrasound imaging system 10. In another embodiment, as shown in FIG. 9, the needle assembly 32 may include a plurality of needle transducers 30 spaced along the length of the needle 34. In alternative embodiments, as shown in FIG. 8, the needle assembly 32 may include multiple needle transducers 30 spaced radially around the needle 34. In such embodiments, orientation of the needle 34 is not relevant (i.e. the needle assembly 32 is not direction sensitive) as the ultrasound probe can easily view one of the radially spaced transducers 30 due to the various radial positions.

Referring back to FIG. 11, rather than utilizing the flexible printed circuit board 46 illustrated in FIG. 7, the needle assembly 32 may include the conduit assembly 56 secured to the exterior surface 40 of the needle 34 from the proximal end 36 to the distal end 38. In such embodiments, the needle assembly 32 may also include at least one electrically-conductive cable 60 extending through the conduit assembly 56 (e.g. extending loosely through the conduit assembly 56 rather than being printed to the surface of the needle 34) so as to electrically connect the needle transducer 35 to the power source 44 of the ultrasound imaging system 10. In such embodiments, the conduit assembly 56 may be constructed of metal tubing, polymer shrink tubing, or any other suitable tubing material. It should be understood that the conduit assembly 56 may define a single lumen 58 or any number of additional lumens such as a double lumen and the lumens may be outside of the needle 34 or inside of the needle 34.

In additional embodiments, the electrically-conductive cable(s) 60 may include a single core wire, a coaxial cable, or any other suitable cable or wire. For example, in one embodiment, the electrically-conductive cable(s) 60 may include a solid- or multi-strand wire, such as an insulated wire of a small gauge (e.g. in the order of 40AWG or smaller). In another embodiment, the electrically-conductive cable(s) 60 may include a coaxial cable of a small gauge (e.g. in the order of 40AWG or smaller) so as to provide a better noise immunity environment. In such embodiments, the lumen 58 of the conduit assembly 56 may be up to about 0.5 mm, such as about 0.25 mm.

It should also be understood that interconnection of the various electrical connections described herein (e.g. the flexible printed circuit board 46 and/or the conduit assembly 56/cables 60) and the needle transducer 35 can be achieved via a variety of methods, including for example via soldering or using a conductive epoxy joint, i.e. with or without a polychlorinated biphenyl (PCB) interface, which can be used to wire bond to the device rather than connecting directly to the wire/cable.

Referring now to FIG. 12, a flow diagram of one embodiment of a method for identifying a needle of a needle assembly on a display screen is illustrated according to the present disclosure. In general, the method 100 will be described herein with reference to the autonomous ultrasound imaging system 10 and the needle assembly 32 shown in FIGS. 1-11 and 13-16. However, in other embodiments, the method 100 may be used in connection with any other suitable autonomous ultrasound imaging system and needle assembly configuration. It should be appreciated that, although FIG. 12 depicts steps or functions performed in a particular order for purposes of illustration and discussion, the steps discussed herein are not limited to any particular order or arrangement. One skilled in the art, using the disclosures provided herein, will appreciate that various steps or functions of the methods disclosed herein can be omitted, rearranged, combined, and/or adapted in various ways without deviating from the scope of the present disclosure.

In one embodiment, it should be understood that the method 100 may include inserting the needle 34 of the needle assembly 32 into a patient, generating, e.g. via the ultrasound probe 30 and/or the needle assembly 32, ultrasound waves that include the needle 34, and then subsequently generating, via the display screen, an image of the needle 34 inserted within the patient based on the ultrasound waves. In other words, the needle assembly 32 is configured to generate its own ultrasound waves to trick the ultrasound imaging system 10 into thinking the waves are reflected signals from the ultrasound probe 30.

Thus, as shown at 102 in FIG. 12, the method 100 includes receiving, via the processor 48 of the needle assembly 32, data signals 45 from the autonomous ultrasound imaging system 10 that include, for example, information relating to ultrasound waves generated by the ultrasound probe 30. In several embodiments, the method 100 may include monitoring the data signals 45 from the autonomous ultrasound imaging system 10 in real-time.

Referring still to FIG. 12, as shown at 104, the method 100 also includes generating, via the needle transducer 35 of the needle assembly 35, a location signal 68 for at least one portion of the needle 34 based on the data signals 45 from the autonomous ultrasound imaging system 10. More specifically, as shown in FIG. 14, the processor(s) 48 may be configured to determine a threshold 70 for the received data signals 45. Thus, as shown, the processor(s) 48 may also be configured to identify a plurality of peak amplitudes 72 within the data signals 45, e.g. based on when the data signals exceed the threshold 70.

Referring back to FIG. 12, as shown at 106, the method 100 also includes modifying, via the processor 48, at least one characteristic of the location signal 68 so as to improve visibility of the location signal on the display screen, wherein the modified location signal 68 is displayed on the display screen during use of the needle assembly so as to locate the at least one portion of the needle 34. For example, in one embodiment, the modified characteristic(s) of the location signal 68 as described herein may include, for example, color, shape, size, brightness, intensity, rate of flashing, echogenicity, and/or other suitable characteristic of the signal 68. For example, as shown in FIG. 13, the location signal 68 is shown on the display screen 18 as being illuminated at the distal end 38 of the needle 34. Thus, in particular embodiments, the location signal 68 may include a periodically flashing marker, a reflective marker coinciding with the at least one portion of the needle 34, and/or any other suitable distinctive marker at the distal end 38 of the needle 34.

In certain embodiments, the processor 48 is configured to pulse the location signal 68 at a known pulse rate and use the known pulse rate to extract the location signal 68 from ultrasound signal noise. In other words, by pulsing the location signal 68 at the known pulse rate, the signal-to-noise ratio of the location signal 68 can be increased as compared to other data signals such that it can be easily extracted and modified. As such, the processor 48 can easily modify the characteristic(s) of the location signal 68 by extracting multiple pulsed location signals 68 from ultrasound noise and processing the collected pulsed location signals 68. In such embodiments, processing the collected pulsed location signals 68 may include, for example, filtering the collected pulsed location signals 68, transforming one or more of the collected pulsed location signals 68, and/or removing outliers from the collected pulsed location signals 68. Thus, the processor 48 can then modify and/or replace the location signal 68 with a different marker to improve visibility/contrast/shape on the display screen.

In additional embodiments, as shown in FIG. 3, the display screen 18 may be part of the autonomous ultrasound imaging system 10. In alternative embodiments, as shown, the display screen 17 may be part of the add-on system 15 to the autonomous ultrasound imaging system 10.

The method 100 of the present disclosure may be better understood with respect to FIGS. 15 and 16. For example, as shown in FIG. 15, a flow diagram of one embodiment of process for identifying the needle 34 of the needle assembly 32 on a display screen according to the present disclosure is illustrated. FIG. 16 illustrates a flow diagram of one embodiment for determining a meta-frame repeat period of an autonomous ultrasound imaging system according to the present disclosure. FIG. 17 illustrates a graph of amplitude (y-axis) versus time (x-axis) that includes one embodiment of a plurality of ultrasound bursts 114 according to the present disclosure. For example, for certain ultrasound machines, the meta-frame rate 110 (e.g. T) generally includes a collection of sub-frames 112 (e.g. t1, t2, t3, etc.). Therefore, in such embodiments, the meta-frame rate 110 may be equal to the number of frames per a specific time period (e.g. seconds). In this instance, the meta-frame rate 110 is equal to three frames per second, assuming T equals one second. In other ultrasound machines, the sub-frames may all be equal (e.g. T=t1=t2=t3. In such embodiments, the meta-frame rate is synonymous with the frame rate.

Referring particularly to FIG. 15, the processor(s) 48 described herein receives the data signals 45 from the transducer 35. As shown at 74, the processor(s) 48 can then process the data signals 45, e.g. using various analog-to-digital converters, filtering, etc. In addition, as shown, the processor(s) 48 may then time stamp 76 the data signals 45, e.g. using a clock 78 or similar.

As shown at 80 and 82, the processor(s) 48 can then determine a baseline noise for the data signals 45 as well as the peak amplitudes of the data signals 45. Thus, as shown at 84, the processor(s) 48 can then set the threshold 70 by accounting for the baseline noise 80 and considering the peak amplitudes 82. In certain embodiments, as shown, a gain 86 can eventually be applied to the received data signals 45, i.e. after the peak amplitudes 82 have been determined. Thus, as shown at 88, the processor(s) 48 can then select the trigger points corresponding the to the peak amplitudes 82. In addition, as shown at 90, the processor(s) 48 is also configured to determine a meta-frame repeat period of the data signals 45. In such embodiments, as shown, the processor(s) 48 may also time stamp 76 the baseline noise 80, the peak amplitudes 82, the meta-frame repeat periods 90, and/or the trigger points 88.

More specifically, as shown in FIG. 16, various process steps for determining the meta-frame repeat period (frame rate) 90 of the data signals 45 according to the present disclosure are illustrated. As shown, in one embodiment, the processor(s) 48 is configured to receive and store the trigger points 88 in a memory device 83. In particular embodiments, as shown, the memory device 83 may periodically discard old data 85. In addition, as shown, the processor(s) 48 may also determine, e.g. via difference calculator 87, a time frame (see e.g. t1, t2, t3 in FIG. 17) between the stored trigger points 88 (peak amplitudes 82). Thus, as shown, the processor(s) 48 may also maintain a record of the time frames between each of the peaks 82, e.g. via sorted store 89. In certain embodiments, the processor(s) 48 may also optionally apply an arithmetic correlation (e.g. a binary correlation) to the record of the time frames. Accordingly, the processor(s) 48 can then determine the meta-frame spacing 90 (e.g. T in FIG. 17) of the autonomous ultrasound imaging system 10 based on the record of the time frames. As such, the present disclosure can be used with any brand of ultrasound imaging system having different meta-frames and/or sub-frames.

Referring back to FIG. 15, the processor(s) 48 is further configured to add a time offset 92 for the data signals 45 based on the meta-frame repeat period 90. In other words, by adding the time offset 92, the processor(s) 48 is configured to anticipate a future frame rate of the autonomous ultrasound imaging system 10. Thus, as shown at 94, the processor(s) 48 is configured to trigger a transmission event. More specifically, as shown at 96, the processor(s) 48 is configured to signal to the needle transducer 35 of the needle assembly 32 to pulse or flash so as to display the location signal 68 on the needle 34 on the display screen.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for identifying a needle of a needle assembly on a display screen, the method comprising:

receiving, via a needle transducer of the needle assembly having a first power source and a first processor, data signals from an autonomous ultrasound imaging system having a second power source and a second processor that operate separately from the first power source and the first processor of the needle assembly, the data signals comprising information relating to a plurality of ultrasound waves generated by an ultrasound probe of the autonomous ultrasound imaging system, wherein the needle transducer is mounted within a recess of the needle on an exterior surface of the needle assembly;

generating, via the first processor of the needle assembly, a location signal for at least one portion of the needle based on the data signals from the autonomous ultrasound imaging system, wherein generating the location signal for the at least one portion of the needle based on the data signals from the autonomous ultrasound imaging system further comprises:

determining, via the first processor of the needle assembly, a threshold for the data signals;
        identifying, via the first processor, a plurality of peak amplitudes within the data signals based on when the data signals exceed the threshold;
        determining a meta-frame rate of the data signals, wherein determining the meta-frame rate of the data signals further comprises: determining a time frame between the plurality of peak amplitudes, maintaining a record of the time frames between each of the plurality of peaks, and determining the meta-frame rate of the autonomous ultrasound imaging system based on the record of the time frames;
        determining a time offset for the data signals based on the meta-frame rate;
        anticipating a future frame rate of the autonomous ultrasound imaging system based on the time offset; and
        signaling to the needle transducer of the needle assembly to flash so as to display the location signal at the at least one portion of the needle on the display screen in anticipation of the future frame rate;

modifying, via the first processor of the needle assembly, at least one characteristic of the location signal so as to improve visibility of the location signal on the display screen; and displaying the modified location signal on the display screen on the at least one portion of the needle during use of the needle assembly so as to locate the at least one portion of the needle.

2. The method of claim 1, wherein determining the threshold for the data signals further comprises determining a baseline noise for the data signals and subsequently determining the threshold for the data signals by eliminating the baseline noise from the data signals.

3. The method of claim 1, wherein determining the meta-frame rate of the data signals further comprises applying an arithmetic correlation to the record of the time frames.

4. The method of claim 1, further comprising:
    pulsing the location signal at a known pulse rate; and
    using the known pulse rate to extract the location signal from ultrasound signal noise.

5. The method of claim 4, wherein modifying the at least one characteristic of the location signal further comprises:
    collecting multiple pulsed location signals; and
    processing the collected pulsed location signals via at least one of filtering the collected pulsed location signals, transforming one or more of the collected pulsed location signals, or removing outliers from the collected pulsed location signals.

6. The method of claim 1, wherein the at least one characteristic of the location signal comprises at least one of color, shape, size, brightness, intensity, rate of flashing, or echogenicity.

7. The method of claim 1, wherein the location signal comprises at least one of a flashing signal or a reflective signal at the at least one portion of the needle.

8. The method of claim 1, wherein the at least one portion of the needle comprises a distal end of the needle.

9. A needle assembly for use with an autonomous ultrasound imaging system, the needle assembly comprising:

a needle comprising a proximal end and a distal end, the distal end adapted to be inserted into a patient; and
    a needle transducer mounted within a recess of the needle on an exterior surface of the needle assembly, the needle transducer configured to receive data signals from the autonomous ultrasound imaging system, the data signals comprising information relating to a plurality of ultrasound waves generated by an ultrasound probe of the autonomous ultrasound imaging system, wherein the needle transducer has a first power source and a first processor, wherein the autonomous ultrasound imaging system has a second power source and a second processor that operates separately from the first power source and the first processor of the needle transducer;

the first processor configured to perform one or more operations, the one or more operations comprising:

generating a location signal for at least one portion of the needle based on the data signals from the autonomous ultrasound imaging system, wherein generating the location signal for the at least one portion of the needle based on the data signals from the autonomous ultrasound imaging system further comprises:

determining a threshold for the data signals;

identifying a plurality of peak amplitudes within the data signals based on when the data signals exceed the threshold;

determining a meta-frame rate of the data signals, wherein determining the meta- frame rate of the data signals further comprises: determining a time frame between the plurality of peak amplitudes, maintaining a record of the time frames between each of the plurality of peaks, and determining the meta-frame rate of the autonomous ultrasound imaging system based on the record of the time frames;

determining a time offset for the data signals based on the meta-frame rate;

anticipating a future frame rate of the autonomous ultrasound imaging system based on the time offset; and signaling to the needle transducer of the needle assembly to flash so as to display the location signal at the at least one portion of the needle on a display screen in anticipation of the future frame rate; and modifying at least one characteristic of the location signal so as to improve visibility of the location signal on the display screen, wherein the modified location signal is displayed on the display screen on the at least one portion of the needle during use of the needle assembly so as to locate the at least one portion of the needle.

10. The needle assembly of claim 9, wherein determining the threshold for the data signals further comprises determining a baseline noise for the data signals and subsequently determining the threshold for the data signals by eliminating the baseline noise from the data signals.

11. The needle assembly of claim 9, wherein determining the meta-frame rate of the data signals further comprises applying an arithmetic correlation to the record of the time frames.

12. The needle assembly of claim 9, further comprising:
pulsing the location signal at a known pulse rate; and
using the known pulse rate to extract the location signal from ultrasound signal noise.

13. The needle assembly of claim 12, wherein modifying the at least one characteristic of the location signal further comprises:
collecting multiple pulsed location signals; and
processing the collected pulsed location signals via at least one of filtering the collected pulsed location signals, transforming one or more of the collected pulsed location signals, or removing outliers from the collected pulsed location signals.

14. The needle assembly of claim 9, wherein the at least one characteristic of the location signal comprises at least one of color, shape, size, brightness, intensity, rate of flashing, or echogenicity.

* * * * *